(12) United States Patent
McKay

(10) Patent No.: US 9,585,764 B2
(45) Date of Patent: Mar. 7, 2017

(54) BONE IMPLANT DEVICE

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 264 days.

(21) Appl. No.: 13/559,105

(22) Filed: Jul. 26, 2012

(65) Prior Publication Data

US 2014/0031937 A1     Jan. 30, 2014

(51) Int. Cl.
*A61F 2/44*     (2006.01)
*A61F 2/28*     (2006.01)
*A61F 2/30*     (2006.01)

(52) U.S. Cl.
CPC .......... *A61F 2/4455* (2013.01); *A61F 2/4465* (2013.01); *A61F 2002/2817* (2013.01); *A61F 2002/2835* (2013.01); *A61F 2002/30059* (2013.01); *A61F 2002/30607* (2013.01); *A61F 2002/30971* (2013.01); *A61F 2310/00359* (2013.01)

(58) Field of Classification Search
CPC ........ A61F 2/28; A61F 2/2803; A61F 2/2846; A61F 2/2875; A61F 2002/28; A61F 2002/2803; A61F 2002/2807; A61F 2002/281; A61F 2002/2825; A61F 2002/2835; A61F 2002/2839; A61F 2002/2846; A61F 2002/285; A61F 2002/2853; A61F 2002/2871; A61F 2002/2892; A61F 2002/2896; A61F 2002/2882
USPC ......... 623/17.11–17.16, 23.51, 23.52, 23.55, 623/23.6, 23.61, 23.63
See application file for complete search history.

(56) References Cited

U.S. PATENT DOCUMENTS

| | | | |
|---|---|---|---|
| 4,485,097 A * | 11/1984 | Bell | 424/549 |
| 4,512,038 A * | 4/1985 | Alexander et al. | 623/23.75 |
| 4,678,470 A * | 7/1987 | Nashef et al. | 623/23.63 |
| 4,708,821 A | 11/1987 | Shimokawa et al. | |
| 4,795,467 A * | 1/1989 | Piez et al. | 424/423 |
| 5,053,049 A * | 10/1991 | Campbell | 623/23.63 |
| 5,298,254 A * | 3/1994 | Prewett et al. | 424/422 |
| 5,306,304 A * | 4/1994 | Gendler | 623/23.63 |
| 5,314,476 A * | 5/1994 | Prewett et al. | 623/23.63 |
| 5,356,629 A * | 10/1994 | Sander et al. | 424/422 |
| 5,507,813 A * | 4/1996 | Dowd et al. | 623/23.63 |
| 5,531,791 A * | 7/1996 | Wolfinbarger, Jr. | 623/23.63 |
| 5,556,430 A * | 9/1996 | Gendler | 128/898 |
| 5,585,116 A * | 12/1996 | Boniface et al. | 424/549 |
| 5,899,939 A * | 5/1999 | Boyce et al. | 623/16.11 |
| 6,090,998 A | 7/2000 | Grooms et al. | |
| 6,123,731 A * | 9/2000 | Boyce et al. | 623/23.63 |

(Continued)

OTHER PUBLICATIONS

McKay, Facet Joint Implant Device, U.S. Appl. No. 13/454,596, filed Apr. 24, 2012, Memphis, TN (US).

*Primary Examiner* — Lynnsy Summitt

(57) ABSTRACT

An osteoimplant device is provided. The osteoimplant device includes a body of nondemineralized cortical bone and an outer surface having at least one region including demineralized bone. The osteoimplant device is formable into a shape and size configured for implantation at a surgical site. A disc shaped osteoimplant can be used for a facet joint fusion. A method of treating a patient having a bone defect in a host bone is also provided, the method including inserting the osteoimplant into the bone defect, for example, one associated with a facet joint.

17 Claims, 2 Drawing Sheets

(56) References Cited

U.S. PATENT DOCUMENTS

| | | | |
|---|---|---|---|
| 6,123,781 A | 9/2000 | Shimazawa | |
| 6,189,537 B1* | 2/2001 | Wolfinbarger, Jr. | 128/898 |
| 6,206,923 B1* | 3/2001 | Boyd et al. | 623/17.11 |
| 6,261,586 B1* | 7/2001 | McKay | 424/423 |
| 6,270,528 B1* | 8/2001 | McKay | 623/17.11 |
| 6,277,149 B1* | 8/2001 | Boyle et al. | 623/17.16 |
| 6,294,041 B1* | 9/2001 | Boyce et al. | 156/275.5 |
| 6,371,988 B1* | 4/2002 | Pafford et al. | 623/17.11 |
| 6,383,221 B1* | 5/2002 | Scarborough et al. | 623/17.11 |
| 6,399,693 B1 | 6/2002 | Brennan et al. | |
| 6,409,765 B1* | 6/2002 | Bianchi et al. | 623/17.11 |
| 6,478,825 B1* | 11/2002 | Winterbottom et al. | 623/23.63 |
| 6,530,955 B2* | 3/2003 | Boyle et al. | 623/17.11 |
| 6,547,823 B2* | 4/2003 | Scarborough et al. | 623/17.16 |
| 6,562,073 B2* | 5/2003 | Foley | 623/17.11 |
| 6,576,017 B2* | 6/2003 | Foley et al. | 623/17.16 |
| 6,616,698 B2* | 9/2003 | Scarborough | 623/23.51 |
| 6,638,310 B2* | 10/2003 | Lin et al. | 623/17.11 |
| 6,706,067 B2* | 3/2004 | Shimp et al. | 623/17.11 |
| 6,749,636 B2* | 6/2004 | Michelson | 623/17.16 |
| 6,761,738 B1* | 7/2004 | Boyd | 623/17.11 |
| 6,761,739 B2* | 7/2004 | Shepard | 623/17.16 |
| 6,843,807 B1* | 1/2005 | Boyce et al. | 623/23.51 |
| 6,855,167 B2* | 2/2005 | Shimp et al. | 623/17.11 |
| 6,863,694 B1* | 3/2005 | Boyce et al. | 623/23.63 |
| 6,911,045 B2* | 6/2005 | Shimp | 623/17.13 |
| 6,913,621 B2* | 7/2005 | Boyd et al. | 623/17.11 |
| 6,991,654 B2* | 1/2006 | Foley | 623/17.16 |
| 7,014,659 B2* | 3/2006 | Boyer et al. | 623/17.15 |
| 7,044,968 B1* | 5/2006 | Yaccarino et al. | 623/16.11 |
| 7,087,082 B2* | 8/2006 | Paul et al. | 623/17.11 |
| 7,217,293 B2* | 5/2007 | Branch, Jr. | 623/17.16 |
| 7,238,203 B2* | 7/2007 | Bagga | A61F 2/442 623/17.11 |
| 7,323,011 B2* | 1/2008 | Shepard et al. | 623/17.11 |
| 7,354,452 B2* | 4/2008 | Foley | A61F 2/446 623/17.11 |
| 7,435,262 B2* | 10/2008 | Michelson | 623/17.16 |
| 7,455,692 B2* | 11/2008 | Michelson | 623/17.11 |
| 7,473,277 B2* | 1/2009 | Boyer et al. | 623/17.15 |
| 7,476,252 B2* | 1/2009 | Foley | 623/17.16 |
| 7,479,160 B2* | 1/2009 | Branch et al. | 623/17.11 |
| 7,498,041 B2 | 3/2009 | Masinaei et al. | |
| 7,500,991 B2* | 3/2009 | Bartish et al. | 623/17.11 |
| 7,537,617 B2 | 5/2009 | Bindsell et al. | |
| 7,540,882 B2* | 6/2009 | Michelson | 623/17.11 |
| 7,563,455 B2* | 7/2009 | McKay | 424/428 |
| 7,575,580 B2* | 8/2009 | Lim et al. | 606/99 |
| 7,611,536 B2* | 11/2009 | Michelson | 623/17.11 |
| 7,615,078 B2* | 11/2009 | White et al. | 623/17.16 |
| 7,618,460 B2* | 11/2009 | Boyd | 623/17.16 |
| 7,637,953 B2* | 12/2009 | Branch et al. | 623/17.11 |
| 7,662,184 B2* | 2/2010 | Edwards et al. | 623/17.11 |
| 7,662,185 B2* | 2/2010 | Alfaro et al. | 623/17.16 |
| 7,662,186 B2* | 2/2010 | Bagga et al. | 623/17.16 |
| 7,678,149 B2* | 3/2010 | Bianchi et al. | 623/17.16 |
| 7,723,395 B2* | 5/2010 | Ringeisen et al. | 521/50 |
| 7,726,002 B2* | 6/2010 | Shimp et al. | 29/525.01 |
| 7,749,270 B2* | 7/2010 | Peterman | 623/17.11 |
| 7,776,095 B2* | 8/2010 | Peterman et al. | 623/17.16 |
| 7,815,682 B1 | 10/2010 | Peterson et al. | |
| 7,833,245 B2* | 11/2010 | Kaes et al. | 606/246 |
| 7,875,075 B2* | 1/2011 | Schwab | 623/17.11 |
| 7,879,103 B2* | 2/2011 | Gertzman et al. | 623/17.16 |
| 7,879,109 B2* | 2/2011 | Borden et al. | 623/23.76 |
| 7,887,594 B2* | 2/2011 | Berry et al. | 623/17.16 |
| 7,935,149 B2* | 5/2011 | Michelson | 623/17.16 |
| 7,938,857 B2* | 5/2011 | Garcia-Bengochea et al. | 623/17.11 |
| 7,939,108 B2* | 5/2011 | Morris et al. | 424/549 |
| 7,967,863 B2* | 6/2011 | Frey et al. | 623/17.11 |
| 7,981,156 B2* | 7/2011 | Pafford et al. | 623/17.11 |
| 7,988,734 B2* | 8/2011 | Peterman et al. | 623/17.11 |
| 7,993,403 B2* | 8/2011 | Foley et al. | 623/17.11 |
| 7,993,406 B2* | 8/2011 | Bianchi et al. | 623/17.16 |
| 7,998,207 B2* | 8/2011 | McKay | 623/17.11 |
| 7,998,209 B2* | 8/2011 | Branch et al. | 623/17.11 |
| 7,998,212 B2* | 8/2011 | Schwab et al. | 623/17.16 |
| 8,002,813 B2* | 8/2011 | Scarborough et al. | 606/331 |
| 8,012,210 B2* | 9/2011 | Lin et al. | 623/17.12 |
| 8,057,545 B2* | 11/2011 | Hughes et al. | 623/17.11 |
| 8,062,365 B2* | 11/2011 | Schwab | 623/17.11 |
| 8,133,421 B2 | 3/2012 | Boyce et al. | |
| 8,137,403 B2* | 3/2012 | Michelson | 623/17.11 |
| 8,182,532 B2* | 5/2012 | Anderson et al. | 623/17.11 |
| 8,187,304 B2* | 5/2012 | Malek | 606/247 |
| 8,197,474 B2* | 6/2012 | Scarborough et al. | 606/33 |
| 8,202,539 B2* | 6/2012 | Behnam et al. | 424/488 |
| 8,221,501 B2* | 7/2012 | Eisermann et al. | 623/17.11 |
| 8,252,055 B2* | 8/2012 | McKay | 623/17.11 |
| 8,262,737 B2* | 9/2012 | Bagga et al. | 623/17.16 |
| 8,268,000 B2* | 9/2012 | Waugh et al. | 623/17.16 |
| 8,308,804 B2* | 11/2012 | Krueger | 623/17.16 |
| 8,308,805 B2* | 11/2012 | Lynn et al. | 623/17.16 |
| 8,328,876 B2* | 12/2012 | Behnam et al. | 623/23.63 |
| 8,343,224 B2* | 1/2013 | Lynn et al. | 623/17.16 |
| 8,349,011 B2* | 1/2013 | Foley | 623/17.11 |
| 8,357,384 B2* | 1/2013 | Behnam et al. | 424/422 |
| 8,372,157 B2* | 2/2013 | Petersen et al. | 623/23.61 |
| 8,389,588 B2* | 3/2013 | Ringeisen et al. | 521/50 |
| 8,403,990 B2* | 3/2013 | Dryer et al. | 623/17.15 |
| 8,403,991 B2* | 3/2013 | Ullrich et al. | 623/17.16 |
| 8,425,604 B2* | 4/2013 | Trieu | 623/17.11 |
| 8,425,607 B2* | 4/2013 | Waugh et al. | 623/17.16 |
| 8,435,566 B2* | 5/2013 | Behnam et al. | 424/488 |
| 8,445,554 B2* | 5/2013 | Ringeisen et al. | 521/50 |
| 2001/0010021 A1* | 7/2001 | Boyd et al. | 623/17.13 |
| 2001/0020186 A1* | 9/2001 | Boyce et al. | 623/17.16 |
| 2001/0032017 A1* | 10/2001 | Alfaro et al. | 623/17.11 |
| 2002/0120338 A1 | 8/2002 | Boyer, II et al. | |
| 2003/0009222 A1* | 1/2003 | Fruh et al. | 623/17.11 |
| 2003/0009235 A1 | 1/2003 | Manrique et al. | |
| 2003/0023305 A1* | 1/2003 | McKay | 623/17.11 |
| 2003/0028197 A1* | 2/2003 | Hanson et al. | 606/99 |
| 2003/0036798 A1* | 2/2003 | Alfaro et al. | 623/17.16 |
| 2003/0060825 A1* | 3/2003 | Alfaro et al. | 606/61 |
| 2003/0083747 A1* | 5/2003 | Winterbottom et al. | 623/17.11 |
| 2003/0114936 A1* | 6/2003 | Sherwood et al. | 623/23.58 |
| 2003/0135275 A1* | 7/2003 | Garcia et al. | 623/17.11 |
| 2003/0139812 A1* | 7/2003 | Garcia et al. | 623/17.11 |
| 2003/0139815 A1* | 7/2003 | Grooms et al. | 623/17.11 |
| 2003/0167092 A1* | 9/2003 | Foley | 623/17.11 |
| 2003/0195629 A1* | 10/2003 | Pafford et al. | 623/17.16 |
| 2003/0195632 A1* | 10/2003 | Foley et al. | 623/17.16 |
| 2004/0030388 A1* | 2/2004 | Null et al. | 623/17.11 |
| 2004/0133279 A1* | 7/2004 | Krueger et al. | 623/17.16 |
| 2004/0146543 A1 | 7/2004 | Shimp et al. | |
| 2004/0210313 A1* | 10/2004 | Michelson | 623/17.11 |
| 2004/0215341 A1* | 10/2004 | Sybert et al. | 623/13.17 |
| 2004/0230309 A1* | 11/2004 | DiMauro et al. | 623/17.12 |
| 2004/0243242 A1* | 12/2004 | Sybert et al. | 623/17.16 |
| 2005/0021142 A1 | 1/2005 | Ganz et al. | |
| 2005/0080486 A1* | 4/2005 | Fallin et al. | 623/17.11 |
| 2005/0085922 A1 | 4/2005 | Shappley et al. | |
| 2005/0143740 A1* | 6/2005 | Morris et al. | 606/69 |
| 2005/0177237 A1* | 8/2005 | Shappley et al. | 623/17.11 |
| 2005/0216085 A1* | 9/2005 | Michelson | 623/17.11 |
| 2005/0256582 A1* | 11/2005 | Ferree | 623/17.16 |
| 2006/0034769 A1 | 2/2006 | Kohn et al. | |
| 2006/0178752 A1* | 8/2006 | Yaccarino et al. | 623/23.63 |
| 2006/0229723 A1* | 10/2006 | Van Hoeck | 623/17.11 |
| 2006/0233851 A1 | 10/2006 | Simon et al. | |
| 2006/0241763 A1* | 10/2006 | Paul et al. | 623/17.11 |
| 2006/0276790 A1 | 12/2006 | Dawson et al. | |
| 2006/0280803 A1 | 12/2006 | Kumar et al. | |
| 2006/0293757 A1 | 12/2006 | McKay et al. | |
| 2007/0032872 A1* | 2/2007 | Simonton et al. | 623/17.11 |
| 2007/0077267 A1* | 4/2007 | Molz et al. | 424/423 |
| 2007/0093912 A1* | 4/2007 | Borden | 623/23.75 |
| 2007/0098756 A1 | 5/2007 | Behnam | |
| 2007/0118220 A1* | 5/2007 | Liu et al. | 623/17.11 |
| 2007/0118222 A1* | 5/2007 | Lang | 623/17.12 |
| 2007/0150064 A1* | 6/2007 | Ruberte et al. | 623/17.16 |
| 2007/0162132 A1* | 7/2007 | Messerli | 623/17.11 |

(56) References Cited

U.S. PATENT DOCUMENTS

| | | | |
|---|---|---|---|
| 2007/0168030 A1* | 7/2007 | Edwards | A61L 27/3608 623/17.11 |
| 2007/0233248 A1* | 10/2007 | Schwab et al. | 623/17.11 |
| 2007/0233272 A1* | 10/2007 | Boyce | A61B 17/0401 623/23.63 |
| 2007/0250166 A1 | 10/2007 | McKay | |
| 2007/0270967 A1* | 11/2007 | Fallin et al. | 623/17.11 |
| 2008/0103602 A1* | 5/2008 | Berry et al. | 623/17.16 |
| 2008/0114465 A1* | 5/2008 | Zanella et al. | 623/23.6 |
| 2008/0154379 A1* | 6/2008 | Steiner et al. | 623/17.16 |
| 2008/0161927 A1* | 7/2008 | Savage et al. | 623/17.16 |
| 2008/0167686 A1* | 7/2008 | Trieu et al. | 606/249 |
| 2008/0195211 A1* | 8/2008 | Lin et al. | 623/17.16 |
| 2008/0215093 A1* | 9/2008 | Lin et al. | 606/246 |
| 2008/0249569 A1* | 10/2008 | Waugh et al. | 606/249 |
| 2008/0255666 A1* | 10/2008 | Fisher et al. | 623/17.16 |
| 2008/0281431 A1 | 11/2008 | Missos | |
| 2009/0062917 A1* | 3/2009 | Foley et al. | 623/17.16 |
| 2009/0099661 A1* | 4/2009 | Bhattacharya et al. | 623/17.16 |
| 2009/0130173 A1* | 5/2009 | Behnam | A61L 27/3604 424/426 |
| 2009/0155378 A1 | 6/2009 | Behnam et al. | |
| 2009/0187247 A1* | 7/2009 | Metcalf et al. | 623/17.16 |
| 2009/0192474 A1 | 7/2009 | Wei et al. | |
| 2009/0270992 A1* | 10/2009 | Gerber et al. | 623/17.16 |
| 2009/0319045 A1 | 12/2009 | Truncale et al. | |
| 2010/0004752 A1* | 1/2010 | White et al. | 623/17.16 |
| 2010/0042216 A1* | 2/2010 | Kilpela et al. | 623/17.11 |
| 2010/0042221 A1* | 2/2010 | Boyd | 623/17.16 |
| 2010/0114175 A1 | 5/2010 | McKay | |
| 2010/0121378 A1* | 5/2010 | Malek | 606/247 |
| 2010/0168798 A1* | 7/2010 | Clineff | A61L 27/446 606/279 |
| 2010/0179658 A1* | 7/2010 | Freeman et al. | 623/17.12 |
| 2010/0234952 A1* | 9/2010 | Peterman | 623/17.11 |
| 2010/0262245 A1* | 10/2010 | Alfaro et al. | 623/17.16 |
| 2010/0268232 A1 | 10/2010 | Betz et al. | |
| 2010/0268341 A1* | 10/2010 | Dvorak et al. | 623/17.12 |
| 2010/0286780 A1* | 11/2010 | Dryer et al. | 623/17.11 |
| 2010/0286783 A1 | 11/2010 | Lechmann et al. | |
| 2011/0004307 A1* | 1/2011 | Ahn | A61F 2/441 623/17.12 |
| 2011/0004311 A1* | 1/2011 | Semler et al. | 623/17.16 |
| 2011/0015741 A1* | 1/2011 | Melkent et al. | 623/17.11 |
| 2011/0054614 A1* | 3/2011 | Morris et al. | 623/17.16 |
| 2011/0054615 A1* | 3/2011 | Buckland et al. | 623/17.11 |
| 2011/0098819 A1 | 4/2011 | Eisermann et al. | |
| 2011/0112643 A1* | 5/2011 | Schwab | 623/17.11 |
| 2011/0144766 A1 | 6/2011 | Kale et al. | |
| 2011/0166655 A1* | 7/2011 | Michelson | 623/17.11 |
| 2011/0172777 A1* | 7/2011 | Sybert et al. | 623/17.16 |
| 2011/0184520 A1* | 7/2011 | Trieu | 623/17.11 |
| 2011/0208311 A1* | 8/2011 | Janowski | 623/17.16 |
| 2011/0208313 A1* | 8/2011 | Michelson | 623/17.16 |
| 2011/0218633 A1* | 9/2011 | Frey et al. | 623/17.16 |
| 2011/0238181 A1* | 9/2011 | Trieu | 623/17.11 |
| 2011/0270402 A1* | 11/2011 | Frey et al. | 623/17.16 |
| 2011/0276138 A1* | 11/2011 | Sherman et al. | 623/17.11 |
| 2011/0282392 A1* | 11/2011 | Murphy et al. | 606/279 |
| 2011/0295372 A1* | 12/2011 | Peterman et al. | 623/17.16 |
| 2012/0041444 A1 | 2/2012 | Einhorn | |
| 2012/0136441 A1* | 5/2012 | Yang et al. | 623/17.11 |
| 2012/0141599 A1* | 6/2012 | Johns et al. | 424/618 |
| 2012/0197402 A1* | 8/2012 | Blackwell et al. | 623/17.16 |
| 2012/0271418 A1* | 10/2012 | Hollister et al. | 623/17.11 |
| 2012/0330423 A1* | 12/2012 | Lin et al. | 623/17.16 |
| 2013/0096686 A1* | 4/2013 | Foley | 623/17.16 |
| 2013/0123927 A1* | 5/2013 | Malandain | 623/17.16 |
| 2013/0131812 A1* | 5/2013 | Ganey | 623/17.16 |

* cited by examiner

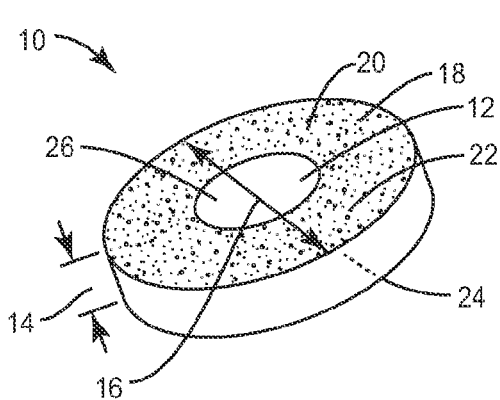
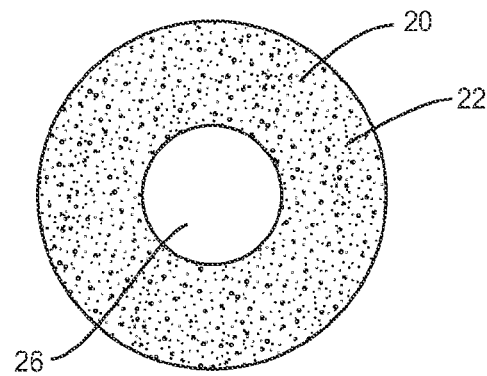
FIG. 2
FIG. 3
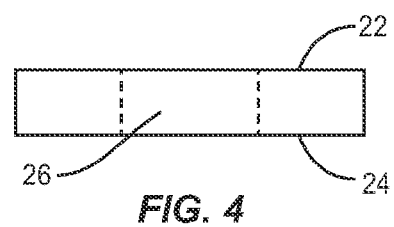
FIG. 4
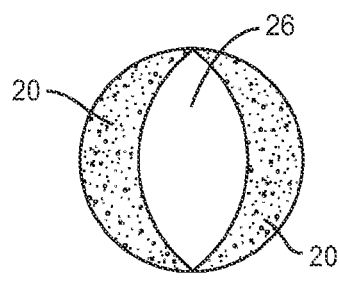
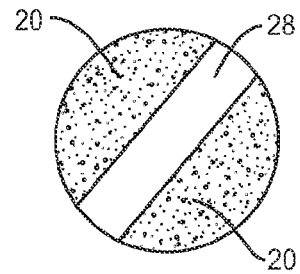
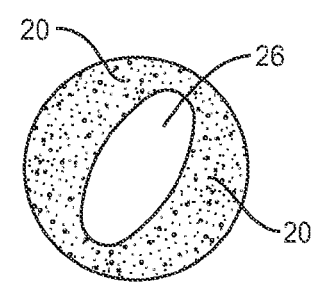
FIG. 5     FIG. 6     FIG. 7

BONE IMPLANT DEVICE

BACKGROUND

The human spine serves many functions. The vertebral members of the spinal column protect the spinal cord. The spinal column also supports other portions of the human body. Furthermore, moveable facet joints and resilient discs disposed between the vertebral members permit motion between individual vertebral members. Each vertebrae includes an anterior body and a posterior arch. The posterior arch includes two pedicles and two laminae that join together to form the spinous process. A transverse process is laterally positioned at the transition from the pedicles to the laminae. Both the spinous process and transverse process provide for attachment of fibrous tissue, including muscle. Two inferior articular processes extend downward from the junction of the laminae and the transverse process. Further, two superior articular processes extend upward from the junction. The articular processes of adjacent vertebrae form the facet joints. The inferior articular process of one vertebra articulates with the superior articular process of the vertebra below. The facet joints are gliding joints because the articular surfaces glide over each other.

Vertebral implants are often used in the surgical treatment of spinal disorders such as degenerative disc disease, disc herniations, curvature abnormalities, and trauma. Many different types of treatments are used. In some cases, spinal fusion is indicated to inhibit relative motion between vertebral bodies. Spinal fusion often involves the removal of the vertebral disc and insertion of an interbody implant to create a fused junction between a pair of vertebral bodies. Furthermore, the facet joints may be fused to complete the fusion between vertebral pairs. Facet fusion often involves destruction of the facet by decorticating the opposing articulating surfaces and packing bone growth promoting substances such as grafts or synthetic materials into the space between the articular processes. The facet joints are generally small as compared to the intervertebral space. Consequently, limited amounts of bone-growth promoting substances may be inserted into the joint. Some of the bone-growth promoting substances tend to disperse post-operatively resulting in a less robust fusion. Furthermore, the overlying fibrous tissue may further disperse the bone-growth promoting substances as a result of contact, friction, and/or the ingrowth of fibrous mass. These and other factors may result in pseudarthrosis or inadequate fusion.

In the spinal surgery field, surgical procedures are often performed to correct problems with displaced, damaged or degenerated intervertebral discs due to trauma, disease or aging. Bone graft materials are often used in spine fusion surgery. Current spinal fusion implants utilize grafts of either bone or artificial implants to fill the intervertebral disc space.

While generally effective, the use of bone grafts has some limitations. Autologous bone grafts, being obtained from the patient, require additional surgery and present increased risks associated with its harvesting, such as risk of infection, blood loss and compromised structural integrity at the donor site. Bone grafts using cortical bone remodel slowly because of their limited porosity. Traditional bone substitute materials and bone chips are more quickly remodeled but cannot immediately provide mechanical support. In addition, while bone substitute materials and bone chips can be used to fill oddly shaped bone defects, such materials are not as well suited for wrapping or resurfacing bone. Indeed, the use of bone grafts is generally limited by the available shapes and sizes of grafts provided.

With regards to bone grafts, allograft bone is a reasonable bone graft substitute for autologous bone. It is readily available from cadavers and avoids the surgical complications and patient morbidity associated with harvesting autologous bone. Allograft bone is essentially a load-bearing matrix comprising cross-linked collagen, hydroxyapatite, and osteoinductive bone morphogenetic proteins. Human allograft tissue is widely used in orthopaedic surgery.

Many approaches using allograft implants in a facet fusion involve mineralized pieces of allograft that are threaded across the joint or impacted into place. These cortical allograft implants can take a very long time to attach and incorporate with the host bone ultimately resulting in a fusion. These allograft implants also require specialized preparation of the facet joint, such as decortication, for the cortical bone implants to fit into place. Many times the preparation of the joint results in the removal of a significant amount of the facet joint leading to further destabilization.

Accordingly, it would be desirable to construct an implant, particularly an interbody implant, to better utilize the benefits of allograft treatment.

SUMMARY

The present disclosure provides an osteoimplant device comprising a nondemineralized cortical bone body having an outer surface. The outer surface has at least one region comprising demineralized bone. The osteoimplant device disclosed herein is formable into a shape and size configured for implantation at a surgical site. In various embodiments, the osteoimplant device is configured as a disc having upper and lower surfaces and containing demineralized regions on both surfaces. In some embodiments, the osteoimplant device can be composite device having two or more components. In some embodiments, the osteoimplant device can be a monolithic device with selective demineralization of the osteoimplant.

In some embodiments, the osteoimplant of this disclosure has a body comprising nondemineralized cortical bone. The nondemineralized cortical bone can be allograft or xenograft in an amount from about 5 wt % to about 95 wt %, from about 15 wt % to about 85 wt %, from about 25 wt % to about 75 wt %, from about 35 wt % to about 65 wt %. In many aspects, the volume of demineralized bone to cortical bone in the osteoimplant device is from about 40 vol % to about 80 vol %, from about 50 vol % to about 70 vol %.

In other embodiments, the osteoimplant device is configured to increase the area contact to the host bone from about 5% to about 60%, from about 10% to about 30%. In various aspects, the host bone is a facet joint.

In certain embodiments, the outer surface of the nondemineralized cortical bone body of the osteoimplant includes at least a region or area of demineralized bone or a demineralized bone matrix. The at least one region of demineralized bone including a demineralized bone matrix can contain demineralized bone matrix fibers and demineralized bone chips in a ratio from about 25:75 to about 75:25 fibers to chips.

In some embodiments the osteoimplant can be generally shaped as a disc or cylinder or any other regular or irregular shape including dome, doughnut, shapes configured for facet joint fusion, shapes configured for posterior lumbar interbody fusion, shapes configured for anterior lumbar interbody fusion or shapes configured for anterior cervical disectomy and fusion.

In various embodiments, the dimensions of the osteoimplant device include a length, a width and a thickness, wherein the thickness of the body is less than at least one of the length and width. The at least one region on the outer surface of the osteoimplant device which contains demineralized bone can have many shapes which can be regular or irregular. In some embodiments, the demineralized regions are shaped patterns including an annular periphery, oblong, circular, curved, triangular, zigzag, substantially crescent, substantially semicircular, substantially O shaped, star, substantially claw-shaped or combinations thereof. The at least one region of demineralized bone can be located anywhere on the upper or lower surfaces or both of the outer surface of the osteoimplant. The location of the demineralized bone region(s) provide flexibility and resilience to the osteoimplant allowing for easy insertion into complicated joints, for example a facet joint. At the same time, the exposure of the joint to mineralized bone facilitates faster fusion at a more anatomical position.

In various embodiments, the osteoimplant device is a disc spacer having a volume of demineralized bone to cortical bone in the implant device is from about 40 vol % to about 80 vol %, from about 50 vol % to about 70 vol %.

In other embodiments, the disc spacer includes nondemineralized cortical bone comprises cortical bone allograft or xenograft in an amount from about 5 wt % to about 95 wt %, from about 15 wt % to about 85 wt %, from about 25 wt % to about 75 wt %, from about 35 wt % to about 65 wt %. The disc spacer is configured to increase the area contact to the host bone from about 5% to about 60%, from about 10% to about 30%.

In various embodiments a method of treating a patient having a bone defect in a host bone is provided. The method includes the step of inserting the osteoimplant device into the bone defect. In certain embodiments, the bone defect is in the facet joint and the osteoimplant configured as a disc is inserted the facet joint for fusion. In some embodiments, the device can be used other than the facet joint, such as for example, in the joints of the knee, ankle, and/or fingers. In other embodiments, the body of nondemineralized cortical bone contacts the load bearing bone tissue of the host bone and the at least one region comprising demineralized bone contacts the non-load bearing bone tissue of the host bone.

While multiple embodiments are disclosed, still other embodiments of the present disclosure will become apparent to those skilled in the art from the following detailed description, which is to be read in connection with the accompanying drawing(s). As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

In part, other aspects, features, benefits and advantages of the embodiments will be apparent with regard to the following description, appended claims and accompanying drawing(s) where:

FIG. 2 is a perspective view of a disc spacer according to one embodiment;

FIG. 3 is a top view of the disc spacer illustrated in FIG. 2;

FIG. 4 is a side view of the disc spacer illustrated in FIG. 2; and

FIGS. 5, 6 and 7 are top views of exemplary bone osteoimplant devices.

DEFINITIONS

Figure 1:
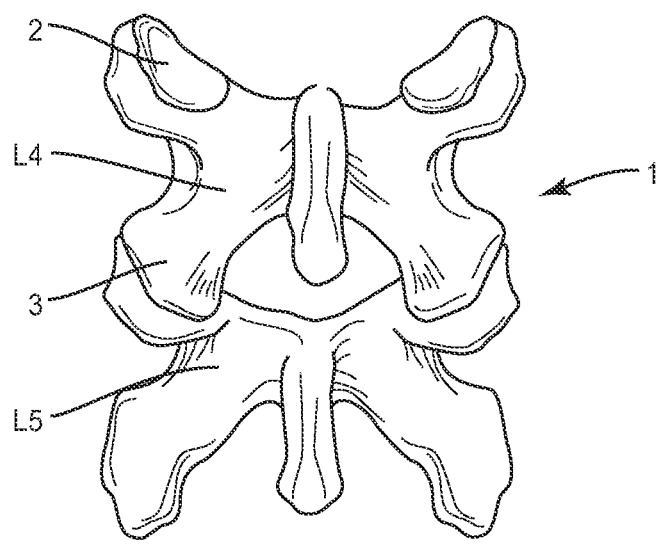
FIG. 1 is a front elevational view of posterior spinal segment illustrating complex facet joints.

To aid in the understanding of the disclosure, the following non-limiting definitions are provided:

"Allograft" as utilized herein refers to tissue, which may be processed to remove cells and/or other components, intended for implantation that is taken from a different member of the same species as the intended recipient. Thus, the term "allograft" includes bone from which substantially all cellular matter has been removed (processed acellular bone) as well as cell-containing bone.

"Autologous" refers to being derived or transferred from the same individual's body, such as for example an autologous bone marrow transplant.

"Bioactive agent or bioactive compound," as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anticholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD.

"Biocompatible," as used herein, refers to materials that, upon administration in vivo, do not induce undesirable long-term effects.

"Bone," as used herein, refers to bone that is cortical, cancellous or cortico-cancellous of autogenous, allogenic, xenogenic, or transgenic origin.

"Composite" as utilized herein refers to the mixture of materials and/or components used in preparing the shaped osteoimplant.

"Demineralized," as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the disclosure. In some embodiments, demineralized bone has less than 95% of its original mineral content. Demineralized is intended to encompass such expressions as "substantially demineralized," "partially demineralized," and "fully demineralized."

"Flexibility" as applied to the demineralized region(s) of the bone-based implant of this invention refers to the characteristic ability, tendency or capacity of the demineralized region(s) of the implant to accommodate, absorb or withstand bending, twisting or torsional forces applied to these region(s), the ability, tendency or capacity being commensurate with the extent and degree of demineralization of the demineralized region(s).

"Resilience" as applied to the demineralized region(s) of the bone-based implant of this invention refers to the characteristic ability, tendency or capacity of the surface(s) of the demineralized region(s) of the implant to accept, or be conformed to, the shape of impressed surface(s), said ability, tendency or capacity being commensurate with the extent and degree of demineralization of the demineralized region(s).

"Demineralized bone matrix" or "DBM" as used herein, refers to any material generated by removing mineral material from bone tissue. In some embodiments, the DBM compositions as used herein include preparations containing less than 5% calcium and preferably less than 1% calcium by weight. Partially demineralized bone (for example, preparations with greater than 5% calcium by weight but containing less than 100% of the original starting amount of calcium) are also considered within the scope of the disclosure.

"Morbidity" refers to the frequency of the appearance of complications following a surgical procedure or other treatment.

"Osteoconductive," as used herein, refers to the ability of a non-osteoinductive substance to serve as a suitable template or substance along which bone may grow.

"Osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

"Osteogenic," as used herein, refers to the ability of an agent, material, or implant to enhance or accelerate the growth of new bone tissue by one or more mechanisms such as osteogenesis, osteoconduction, and/or osteoinduction. To have direct osteogenic activity, the graft must contain cellular components that directly induce bone formation. For example, a collagen matrix seeded with activated mesenchymal stem cells (MSCs) would have the potential to induce bone formation directly, without recruitment and activation of host MSC populations. Because many osteoconductive scaffolds also have the ability to bind and deliver bioactive molecules, their osteoinductive potential will be greatly enhanced.

"Osteoimplant," as used herein, refers to any bone-derived implant prepared in accordance with the embodiments of this disclosure and therefore is intended to include expressions such as bone membrane or bone graft.

"Osteoinductive," as used herein, refers to the quality of being able to recruit cells from the host that have the potential to stimulate new bone formation. Any material that can induce the formation of ectopic bone in the soft tissue of an animal is considered osteoinductive.

"Osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

"Shape" as applied to the osteoimplant herein refers to a determined or regular form or configuration in contrast to an indeterminate or vague form or configuration (as in the case of a lump or other solid mass of no special form) and is characteristic of such materials as sheets, plates, discs, cores, pins, screws, tubes, teeth, bones, portions of bones, wedges, cylinders, threaded cylinders, cages, and the like. This includes forms ranging from regular, geometric shapes to irregular, angled, or non-geometric shapes, and combinations of features having any of these characteristics.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

"Patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

"Treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols, which have only a marginal effect on the patient.

"Xenograft" refers to tissue or organs from an individual of one species transplanted into or grafted onto an organism of another species, genus, or family.

"Xenogenic" as utilized herein refers to material intended for implantation obtained from a donor source of a different species than the intended recipient. For example, when the implant is intended for use in an animal such as a horse (equine), xenogenic tissue of, for example, bovine, porcine, caprine origin may be suitable.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Certain terminology, which may be used in the following description is for convenience only and is not limiting. For example, the words "right", "left", "top" and "bottom" designate directions in the drawings to which reference is made. The words, "anterior", "posterior", "superior", "inferior", "lateral" and related words and/or phrases designate preferred positions and orientations in the human body to which reference is made and are not meant to be limiting. The terminology includes the above-listed words, derivatives thereof and words of similar import.

The present disclosure provides a novel allograft implant, which in some aspects, is specifically designed to fuse a facet joint. The design includes the use of a partially demineralized allograft disc that has some inherent flexibility resulting from the presence of demineralized portions or regions. As a result of this flexibility, the disc can be easily inserted into the complicated 3D curved facet joint shape, as well as facilitate faster fusion by exposing some of the inherent osteogenic factors, such as for example bone morphogenic protein, present in the cortical nondemineralized allograft. The mineralized regions of the osteoimplant described in this disclosure allow for mechanical distraction of the facet joint so fusion can occur at a more anatomical position.

In some embodiments, the osteoimplant device can be composite device having two or more components. In some embodiments, the osteoimplant device can be a monolithic device with selective demineralization of the osteoimplant.

In some embodiments, the allograft having one or more demineralized regions or portions allows some flexibility that allows it to flex in from about 5 to about 45 degree angles or from about 10 degrees to about 20 degrees. Therefore, the allograft can flex to match the complex curvature of the facet joint, knees, and/or fingers.

The present disclosure also provides various exemplary designs of bone implants comprising a composite of nondemineralized cortical allograft bone having regions of demineralized or partially demineralized bone which provide flexibility and resiliency to the resulting osteoimplant. In various embodiments, the use of novel osteoimplant devices according to the present disclosure requires removal of soft tissues from the facet joint and sliding in of the partially demineralized allograft disc. Even though the facet has a somewhat complicated surface geometry, the flexible disc configuration allows for easy insertion due to its partial flexibility. The amount of demineralization and the portion or region of the disc demineralized can be adjusted to give the disc just the right amount of flexibility and strength. The demineralized region will begin facilitating new bone formation relatively fast compared to a solid nondemineralized cortical disc. Accordingly, the entire facet fusion process can be accelerated by inserting the osteoimplant device described in this disclosure into the bone defect present in a facet joint.

One exemplary configuration according to the present disclosure involves providing a composite osteoimplant device comprising a nondemineralized cortical bone body, which includes an outer surface having at least one region having demineralized bone, wherein the implant device is formable into a shape and size configured for implantation at a surgical site.

A body of nondemineralized cortical bone is provided having an outer surface with regions of demineralized bone, which can provide inherent flexibility and resilience to the osteoimplant. This composite design of the body and the outer surface allows for the advantageous properties of each component to be fully realized. According to some embodiments, the composite implant is configured to increase the surface area contact of the allograft with the host bone, which will result in faster fusion and a stronger fusion mass. In some embodiments, as a result of the surface demineralization of the cortical allograft body, osteoinductivity of the osteoimplant increases and fusion with the host bone increases. In some embodiments, because of its high load bearing capability and high compressive strength, the majority of the mechanical load is carried by the nondemineralized allograft. The demineralized portion or region typically has lower compressive strength; however it provides the osteoimplant with enhanced resiliency and flexibility. In some embodiments, part of the surface of the allograft can be demineralized to a depth of from about 50 to about 5000 microns, or about 100 microns to about 1000 microns to provide the desired bone growth in the facet defect.

Advantageously, it is noted that an implant device may be provided in any configuration, size and shape, as per the requirements of the desired target site. The location of the demineralized and mineralized areas of the disc can be strategically located to optimize the insertion and incorporation process of the osteoimplant. It is also possible to have alternate implant shapes different from a disc shape having this selectively demineralized design feature. Thus, an almost unlimited ranges of sizes and shapes of optimized bone osteoimplant devices may be provided. In one example, an implant device may be configured to be adapted for fusion of a facet joint. However, alternate configurations of the implant device are contemplated to suit the needs of a patient's bone graft target site and many other variations on a disc design are possible.

FIG. 1 illustrates a front elevational view of a posterior spinal segment 1 illustrating a superior articular facet joint 2 and an interlocking facet joint 3 associated with lumbar vertebrae L4 and L5. Generally, facet joints link the bones of the spine together in the posterior part of the spine to provide stability to the spine. Each vertebra is associated with four facet joints, a pair that face upward and another pair that face downward.

FIG. 2 depicts a perspective view of one exemplary configuration of the osteoimplant according to principles of the present disclosure. Osteoimplant 10 comprises, consists essentially of, or consists of a body 12 prepared of nondemineralized cortical bone. Configured as a round disc, body 12 has a thickness 14 and a diameter 16. In some embodiments, body 12 can have an elongated shape, for example, cylindrical or rectangular, then body 12 can have thickness, length and width of any dimension suitable for insertion at a selected surgical site. Body 12 has an outer surface 18 having at least one region 20 comprising, consisting essentially of, or consisting of demineralized bone exhibiting flexibility and resilience. FIGS. 3 and 4 depict top and side views, respectively, of the osteoimplant device shown in FIG. 2, wherein outer surface 18 of body 12 can be prepared of nondemineralized cortical bone. As illustrated in FIG. 2, outer surface 18 contains contiguous or noncontiguous regions 20 of demineralized bone on both the upper surface 22 and lower surface 24. Regions 20 can be located anywhere on outer surface 18 of body 12, for example, in a peripheral annular shape around a core 26 of nondemineralized bone.

In other various embodiments, as illustrated in FIGS. 5, 6 and 7, regions 20 of demineralized bone can be located on surface 18 in many other patterns and many other variations are possible. In some aspects, as shown in FIG. 5, regions 20 can be substantially crescent shaped and peripherally located around core 26. In FIG. 6, regions 20 are substantially semicircular and separated by a core shaped as a band 28. In FIG. 7, demineralized regions 20 may be peripherally located in substantially O shaped pattern around a core 26. Regions 20 of outer surface 18 can include other regular or irregular shapes, for example, oval, square, diamond, star, polygonal or non-polygonal.

The nondemineralized bone useful in providing the osteoimplants of this disclosure can be selected to be a section of strong cortical bone such as that obtained from the femur, tibia, fibula, radius, ulna, and the like. The source of the bone for body 12 can be allograft or xenograft with the appropriate cautionary steps known in the art being taken in each case to prevent contamination by pathogenic and/or antigenic agents. The bone unit for body 12 can be obtained from a section of a long bone shaft (such as the aforementioned femur, tibia, radius, ulna, etc.) and is configured, for example, by machining (before or after demineralization and/or the deactivation treatment described below) into the size and shape of the desired prosthetic implant.

Demineralization can be carried out by any of the known and conventional demineralization procedures to reduce the mineral content of at least one surface region 20 of body 12. The demineralized bone is rubbery in feel, which is to say, it possesses properties of flexibility and resilience. In addition, the osteoimplant having a nondemineralized body with a demineralized surface in whole or in part possesses sufficient strength to support the sort of mechanical loads that are typical of bone.

Demineralization methods remove the inorganic mineral component of bone by employing acid solutions. Such methods are well known in the art, see for example, Reddi et al., Proc. Nat. Acad. Sci. 69, pp 1601-1605 (1972), incorporated herein by reference herein. The strength of the acid solution, the shape of the bone particles and the duration of the demineralization treatment will determine the extent of demineralization. Reference in this regard may be made to Lewandrowski et al., J. Biomed Materials Res, 31, pp 365-372 (1996), also incorporated herein by reference.

In one demineralization procedure, the allograft bone of body 12 is subjected to a defatting/disinfecting step, which is followed by an acid demineralization step. A useful defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to about 40 percent by weight of water (or about 60 to about 90 weight percent of defatting agent such as alcohol) should be present in the defatting disinfecting solution to produce optimal lipid removal and disinfection within the shortest period of time. In some embodiments, the concentration range of the defatting solution is from about 60 to about 85 weight percent alcohol and most preferably about 70 weight percent alcohol. Following defatting, the allograft bone of body 12 is immersed in acid over time to effect partial demineralization. Acids which can be employed in this step include inorganic acids such as hydrochloric acid, nitric acid, phosphoric acid and others and organic acids such as peracetic acid, p-toluene sulfonic acid, trifluoroacetic acid and others. After acid treatment, the regions of demineralized bone are rinsed with sterile water to remove residual amounts of acid and thereby raise the pH. The wet surface demineralized bone of body 12 can then be immediately shaped into any desired configuration or stored under aseptic conditions, advantageously in a lyophilized state, for processing at a later time. As an alternative to aseptic processing and storage, the surface demineralized bone of body 12 can be shaped into a desired configuration and sterilized during or after processing using known methods.

Nondemineralized bone present in body 12 possesses an initial and ongoing mechanical role, and later a biological role, in the osteoimplant of this invention. Nondemineralized bone provides stiffness and strength to the osteoimplant and thus enhances its ability to support load. Nondemineralized bone also plays a biological role in bringing about new bone ingrowth by osteoconduction. Thus, the bone osteoimplant is gradually remodeled and replaced by new host bone as incorporation of the osteoimplant progresses over time.

Demineralized bone found in regions on the surface of body 12 also possesses an initial and ongoing mechanical role, and later a biological role, in the osteoimplants described this disclosure. Regions of superficial or partial demineralization bring about new bone ingrowth by osteoinduction.

In various embodiments, in the composite implant device described herein, the nondemineralized cortical bone comprises cortical bone allograft or xenograft in an amount from about 5 wt % to about 95 wt %, from about 15 wt % to about 85 wt %, from about 25 wt % to about 75 wt %, from about 35 wt % to about 65 wt %. In other embodiments, the relative volume of demineralized bone to cortical bone in the osteoimplant device of this disclosure is from about 10 vol % to about 60 vol %, from about 15 vol % to about 40 vol %, from about 20 vol % to about 30 vol %. In one aspect, the relative volume of demineralized bone to cortical bone in the osteoimplant device of this disclosure is from about 15 vol % to about 30 vol %.

Osteoimplants having a nondemineralized body having a surface that has been partially or superficially demineralized will tend to possess a fairly high compressive strength, one approaching that of natural bone. Accordingly, the wet compressive strength of the osteoimplants of this disclosure can be of the order of from about 20 to about 200 MPa. In some embodiments, a compressive strength of such composite materials is about 30, 40, 60, 80, 90, 100, 110, 120, 130, 140, 150, 160, 170, 180, 190 MPa or between any compressive strengths of the above. Where an osteoimplant of lower compressive strength is desired, the regions on the outer surface of body 12 containing partially or fully demineralized bone can be increased. Thus, increasing or decreasing the amount of regions containing partially or fully demineralized bone on the surface of body 12 can be used to control the overall mechanical and biological properties, for example, the strength, osteoconductivity and/or osteoinductivity, of the osteoimplant. The differential in compressive strength, osteogenicity and other properties between partially and/or fully demineralized bone on the one hand and nondemineralized and/or superficially demineralized bone on the other hand can be exploited. For example, nondemineralized and/or superficially demineralized bone can be concentrated in that region of the osteoimplant which will be directly subjected to applied load upon implantation.

In some embodiments, the composite osteoimplants described in this disclosure can have a compressive modulus of about 3800, 3600, 3400, 3200, 3000, 2500, 2000, 1500, 1000, 800, 600, 400, 200 MPa or between any compressive modulus of above.

In some embodiments, the composite implant device is configured to increase the relative surface area contact of demineralized regions and nondemineralized allograft bone to the host bone from about 5% to about 50%, from about 10% to about 20%.

In various embodiments, the at least one region of demineralized bone comprised by the outer surface of the composite osteoimplant of this disclosure includes a demineralized bone matrix including demineralized bone matrix fibers and demineralized bone chips in a ration from about 25:75 to about 75:25 fibers to chips.

In some embodiments, the composite osteoimplant device can comprise an allograft portion that is configured to be joined to another allograft portion. In this way, the composite interbody device can be joined before it is implanted at or neat the target site. The composite interbody implant can have mating surfaces comprising recesses and/or projections and reciprocating recesses and/or projections (for example, joints) that allow the implant to be assembled before implantation. Assembly can also include, for example, use of an adhesive material to join parts of the implant together and provide strong interlocking fit.

The adhesive material may comprise polymers having hydroxyl, carboxyl, and/or amine groups. In some embodiments, polymers having hydroxyl groups include synthetic polysaccharides, such as for example, cellulose derivatives, such as cellulose ethers (for example, hydroxypropylcellulose). In some embodiments, the synthetic polymers having a carboxyl group, may comprise poly(acrylic acid), poly (methacrylic acid), poly(vinyl pyrrolidone acrylic acid-N-hydroxysuccinimide), and poly(vinyl pyrrolidone-acrylic acid-acrylic acid-N-hydroxysuccinimide) terpolymer. For example, poly(acrylic acid) with a molecular weight greater than 250,000 or 500,000 may exhibit particularly good adhesive performance. In some embodiments, the adhesive can be a polymer having a molecular weight of about 2,000 to about 5,000, or about 10,000 to about 20,000 or about 30,000 to about 40,000.

In some embodiments, the adhesive can comprise imido ester, p-nitrophenyl carbonate, N-hydroxysuccinimide ester, epoxide, isocyanate, acrylate, vinyl sulfone, orthopyridyl-disulfide, maleimide, aldehyde, iodoacetamide or a combination thereof. In some embodiments, the adhesive material can comprise at least one of fibrin, a cyanoacrylate (for example, N-butyl-2-cyanoacrylate, 2-octyl-cyanoacrylate), a collagen-based component, a glutaraldehyde glue, a hydrogel, gelatin, an albumin solder, and/or a chitosan adhesives. In some embodiments, the hydrogel comprises acetoacetate esters crosslinked with amino groups or polyethers as mentioned in U.S. Pat. No. 4,708,821. In some embodiments, the adhesive material can comprise poly(hydroxylic) compounds derivatized with acetoacetate groups and/or polyamino compounds derivatized with acetoacetamide groups by themselves or the combination of these compounds crosslinked with an amino-functional crosslinking compounds.

The adhesive can be a solvent based adhesive, a polymer dispersion adhesive, a contact adhesive, a pressure sensitive adhesive, a reactive adhesive, such as for example multi-part adhesives, one part adhesives, heat curing adhesives, moisture curing adhesives, or a combination thereof or the like. The adhesive can be natural or synthetic or a combination thereof.

Contact adhesives are used in strong bonds with high shear-resistance. Pressure sensitive adhesives form a bond by the application of light pressure to bind the adhesive with the target tissue site, cannula and/or expandable member. In some embodiments, to have the device adhere to the target tissue site, pressure is applied in a direction substantially perpendicular to a surgical incision.

Multi-component adhesives harden by mixing two or more components, which chemically react. This reaction causes polymers to cross-link into acrylics, urethanes, and/or epoxies. There are several commercial combinations of multi-component adhesives in use in industry. Some of these combinations are: polyester resin-polyurethane resin; polyols-polyurethane resin, acrylic polymers-polyurethane resins or the like. The multi-component resins can be either solvent-based or solvent-less. In some embodiments, the solvents present in the adhesives are a medium for the polyester or the polyurethane resin. Then the solvent is dried during the curing process.

In some embodiments, the adhesive can be a one-part adhesive. One-part adhesives harden via a chemical reaction with an external energy source, such as radiation, heat, and moisture. Ultraviolet (UV) light curing adhesives, also known as light curing materials (LCM), have become popular within the manufacturing sector due to their rapid curing time and strong bond strength. Light curing adhesives are generally acrylic based. The adhesive can be a heat-curing adhesive, where when heat is applied, such as body heats, the components react and cross-link. This type of adhesive includes epoxies, urethanes, and/or polyimides. The adhesive can be a moisture curing adhesive that cures when it reacts with moisture present (for example, bodily fluid) on the substrate surface or in the air. This type of adhesive includes cyanoacrylates or urethanes. The adhesive can have natural components, such as for example, vegetable matter, starch (dextrin), natural resins or from animals e.g. casein or animal glue. The adhesive can have synthetic components based on elastomers, thermoplastics, emulsions, and/or thermosets including epoxy, polyurethane, cyanoacrylate, or acrylic polymers.

In some embodiments, to improve the osteoinductive properties, it is desirable to use demineralized bone matrix (DBM) as the osteoinductive material present in at least one region 20 on the outer surface 18 of the osteoimplant 10, due to superior biological properties of DBM relative to nondemineralised allograft bone, since the removal of minerals increases the osteoinductivity of the graft. Currently, there are a range of DBM products in clinical use.

Demineralized bone matrix (DBM) is demineralized allograft bone with osteoinductive activity. As discussed above, DBM is prepared by acid extraction of allograft bone, resulting in loss of most of the mineralized component but retention of collagen and noncollagenous proteins, including growth factors. DBM does not contain osteoprogenitor cells, but the efficacy of a demineralized bone matrix as a bone-graft substitute or extender may be influenced by a number of factors, including the sterilization process, the carrier, the total amount of bone morphogenetic protein (BMP) present, and the ratios of the different BMPs present. DBM includes demineralized pieces of cortical bone to expose the osteoinductive proteins contained in the matrix. These activated demineralized bone particles are usually added to a substrate or carrier such as glycerol or a polymer. DBM is mostly an osteoinductive product, but lacks enough induction to be used on its own in challenging healing environments such as posterolateral spine fusion.

According to some embodiments of the disclosure, DBM can comprise demineralized bone matrix fibers and/or demineralized bone matrix chips. In some embodiments, the demineralized bone matrix may comprise demineralized bone matrix fibers and demineralized bone matrix chips in a 30:60 ratio. In certain embodiments, the at least one region of demineralized bone comprised by the outer surface of the composite osteoimplant of this disclosure includes a demineralized bone matrix including demineralized bone matrix fibers and demineralized bone chips in a ration from about 25:75 to about 75:25 fibers to chips.

According to one embodiment of the disclosure, the bone graft materials of the present disclosure include those structures that have been modified in such a way that the original chemical forces naturally present have been altered to attract and bind molecules, including, without limitation, growth factors and/or cells, including cultured cells. Namely, the demineralized allograft bone material may be further modified such that the original chemical forces naturally present have been altered to attract and bind growth factors, other proteins and cells affecting osteogenesis, osteoconduction and osteoinduction. For example, a demineralized allograft bone material may be modified to provide an ionic gradient to produce a modified demineralized allograft bone material, such that implanting the modified demineralized allograft bone material results in enhanced ingrowth of host bone.

In one embodiment an ionic force change agent may be applied to modify the demineralized allograft bone material. The demineralized allograft bone material may comprise, a demineralized bone matrix (DBM) comprising fibers, particles and any combination of thereof.

The ionic force change agent may be applied to the entire demineralized allograft bone material or to selected portions/surfaces thereof. The ionic force change agent may be a binding agent, which modifies the demineralized allograft bone material or bone graft structure to bind molecules, such as, for example, growth factors, or cells, such as, for example, cultured cells, or a combination of molecules and cells. In the practice of the disclosure the growth factors include but are not limited to BMP-2, rhBMP-2, BMP-4, rhBMP-4, BMP-6, rhBMP-6, BMP-7(OP-1), rhBMP-7, GDF-5, LIM mineralization protein, platelet derived growth factor (PDGF), transforming growth factor-β (TGF-β), insulin-related growth factor-I (IGF-I), insulin-related growth factor-II (IGF-II), fibroblast growth factor (FGF), beta-2-microglobulin (BDGF II), and rhGDF-5. A person of ordinary skill in the art will appreciate that the disclosure is not limited to growth factors only. Other molecules can also be employed in the disclosure. For example, tartrate-resistant acid phosphatase, which is not a growth factor, may also be used in the disclosure.

If a cell culture is employed, the cells include but are not limited to mesenchymal stems cells, pluripotent stem cells, osteoprogenitor cells, osteoblasts, osteoclasts, and any bone marrow-derived cell lines.

In some embodiments, the ionic force change agent comprises at least one of enzymes, enzyme mixtures, pressure (for example, isostatic pressure), chemicals, heat, sheer force, oxygen plasma, or a combination thereof. For example, the ionic force change agent may comprise an enzyme such as collagenase or pepsin, which can be administered for a sufficient period of time to partially digest at least a portion of the demineralized allograft bone material. Subsequently, the enzyme may be deactivated and/or removed.

Any enzyme or enzyme mixture may be contemplated, and treatment time durations may be altered in accordance with the enzyme(s) used. Some suitable enzymes that may degrade the DBM material include, but are not limited to, cysteine proteinases, matrix metalloproteinases, enzymes such as amylases, proteases, lipases, pectinases, cellulases, hemicellulases, pentosanases, xylanases, phytases or combinations thereof.

Exemplary enzymes suitable to partially degrade and modify the DBM material, include but are not limited to, cathepsin L, cathepsin K, cathepsin B, collagenase, pepsin, plasminogen, elastase, stromelysin, plasminogen activators, or a combination thereof.

In some embodiments, the DBM material can be subjected to pressure to modify it. The simplest pressing technique is to apply pressure to the unconstrained DBM material. Examples include pressing the DBM material using a mortar and pestle, applying a rolling/pressing motion such as is generated by a rolling pin, or pressing the bone pieces between flat or curved plates. These flattening pressures cause the DBM material fibers to remain intact.

Another pressing technique involves mechanically pressing demineralized bone material, which can be constrained within a sealed chamber having a hole (or a small number of holes) in its floor or bottom plate. The separated fibers extrude through the holes with the hole diameter limiting the maximum diameter of the extruded fibers. This constrained technique results in fibers that are largely intact (as far as length is concerned).

In a combined unconstrained/constrained pressing technique that results in longer fibers by minimizing fiber breakage, the demineralized bone is first pressed into an initially separated mass of fibers while in the unconstrained condition and thereafter these fibers are constrained within the sealed chamber where pressing is continued.

In general, pressing of demineralized bone to provide demineralized bone particles can be carried out at from about 1,000 to about 40,000 psi, and preferably at from about 5,000 to about 20,000 psi.

Subsequent to the addition of the ionic force change agent, the practitioner may optionally administer an appropriate molecule or cell culture. Generally, the molecule or cell culture is applied within minutes, for example from about 1 to about 120 minutes before implantation into the patient.

One class of molecules suitable for one embodiment of the disclosure is growth factors. Growth factors suitable for use in the practice of the disclosure include but are not limited to bone morphogenic proteins, for example, BMP-2, rhBMP-2, BMP-4, rhBMP-4, BMP-6, rhBMP-6, BMP-7 (OP-1), rhBMP-7, GDF-5, and rhGDF-5. Bone morphogenic proteins have been shown to be excellent at growing bone and there are several products being tested. For example, rhBMP-2 delivered on an absorbable collagen sponge (INFUSE® Bone Graft, Medtronic Sofamor Danek, Memphis, Tenn.) has been used inside titanium fusion cages and resulted in successful fusion and can be used on a ceramic carrier to enhance bone growth in a posterolateral fusion procedure. rhBMP-2 can also be used on a carrier for acute, open fractures of the tibial shaft. BMP-7 (OP-1) also enhances bone growth in a posterolateral fusion procedure.

Additionally, suitable growth factors include, without limitation, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), and beta-2-microglobulin (BDGF II).

Further, molecules, which do not have growth factor properties may also be suitable for this disclosure. An example of such molecules is tartrate-resistant acid phosphatase.

In one embodiment, the demineralized allograft bone material is treated with a negatively-charged ionic force change agent to produce a negatively-charged demineralized allograft bone material. The negatively-charged demineralized allograft bone material attracts a positively charged molecule having a pI from about 8 to about 10. Examples of positively charged molecules having a pI from about 8 to about 10 include but are not limited to, rhBMP-2 and rhBMP-6.

In another embodiment, the demineralized allograft bone material is treated with a positively-charged ionic force change agent such that the positively-charged demineralized allograft bone material attracts a molecule with a slightly negative charge, for example a charge of pI about 5 to about 7. Examples of molecules having a slightly negative charge include rhBMP-4.

In yet another embodiment, the demineralized allograft bone material is treated with a positively-charged ionic force change agent to produce a positively-charged demineralized allograft bone material such that cells, in particular cell cultures having a negative surface charge bind to the positively-charged demineralized allograft bone material. Examples of cells, which are suitable for use in the practice of the disclosure include but are not limited to mesenchymal stems cells, pluripotent stem cells, embryonic stem cells, osteoprogenitor cells and osteoblasts.

The mechanisms by which a demineralized allograft bone material may acquire ionic forces include but are not limited to ionization, ion adsorption and ion dissolution.

In one embodiment, the implant is modified to give it the selected charge by a one-to-one substitution of the calcium ion with lithium, sodium, potassium or cesium of hydroxyapatite.

In yet another aspect, treatments with gradient-affecting elements, such as elements present in hydroxyapatite, and human proteins are employed. Suitable gradient-affecting proteins are those present in the organic phase of human bone tissue. The gradient-affecting proteins derive molecule or cell attraction without the potential damaging effects on the implants, as may be the case with other chemical treatments. Usually this is accomplished through surface treatments such as, for example, plasma treatment to apply an electrostatic charge on bone.

The term "plasma" in this context is an ionized gas containing excited species such as ions, radicals, electrons and photons. The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces. Plasma treatment is an effective method to uniformly alter the surface properties of substrates having different or unique size, shape and geometry including but not limited to bone and bone composite materials.

For embodiments where the substance attached to DBM is biologic, the substance may be autogenic, allogenic, xenogenic, or transgenic. However, it is contemplated that other suitable materials may be positioned on the osteoimplant device such as, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. In some embodiments, the substance may be pressed before placement in the implant device. A substance provided within the implant device may be homogenous, or generally a single substance, or may be heterogeneous, or a mixture of substances.

Surface Modifications and Additives

Surface modification may provide a chemical substance that is strongly bonded to the surface of bone, for example, covalently bonded to the surface of the demineralized regions on the outer surface of the osteoimplant device described in this disclosure. Bone particles of DBM may, alternatively or additionally, be coated with a material to facilitate interaction with polymers of composite materials.

In some embodiments, silane coupling agents are employed to link a monomer or initiator molecule to the surface of bone particles present in DBM regions of the osteo implant. Silane has at least two sections, a set of leaving groups and at least an active group. An active group may be connected to the silicon atom in the silane by an elongated tether group. An exemplary silane coupling agent is 3-trimethoxysilylpropylmethacrylate, available from Union Carbide. Three methoxy groups are leaving groups, and the methacrylate active group is connected to the silicon atom by a propyl tether group. In some embodiments, a leaving group is an alkoxy group such as methoxy or ethoxy. Depending on the solvent used to link the coupling agent to bone particles, hydrogen or alkyl groups such as methyl or ethyl may serve as leaving groups. The length of tethers determines the intimacy of connection between polymers and bone particles. By providing a spacer between bone particles and active groups, the tether also reduces competition between chemical groups at the particle surface and the active group and makes the active group more accessible to monomers during polymerization.

In some embodiments, an active group is an analog of monomers of a polymer used in composite materials. For example, amine active groups will be incorporated into polyurethane matrices, copolymers (for example, polyesters, polycarbonates, polycaprolactone), and other polymer classes based on monomers that react with amines, even if the polymer does not contain an amine. Hydroxy-terminated silanes will be incorporated into polyamino acids, polyesters, polycaprolactone, polycarbonates, polyurethanes, and other polymer classes that include hydroxylated monomers. Aromatic active groups or active groups with double bonds will be incorporated into vinyl polymers and other polymers that grow by radical polymerization (for example, polyacrylates, polymethacrylates). It is not necessary that the active group be monofunctional. Indeed, it may be preferable that active groups that are to be incorporated into polymers via step polymerization be difunctional. A silane having two amines, even if one is a secondary amine, will not terminate a polymer chain but can react with ends of two different polymer chains. Alternatively, the active group may be branched to provide two reactive groups in the primary position.

An exemplary list of silanes that may be used with the present invention is provided in U.S. Patent Publication No. 20040146543, the contents of which are incorporated herein by reference. Silanes are available from companies such as Union Carbide, AP Resources Co. (Seoul, South Korea), and BASF. Where a silane contains a potentially non-biocompatible moiety as the active group, it may be used to tether a biocompatible compound to bone particles using a reaction in which the non-biocompatible moiety is a leaving group. It may be desirable to attach the biocompatible compound to the silane before attaching the silane to the bone particle, regardless of whether the silane is biocompatible or not. The derivatized silanes may be mixed with silanes that can be incorporated directly into the polymer and reacted with bone particles, coating the bone particles with a mixture of "bioactive" silanes and "monomer" silanes. U.S. Pat. No. 6,399,693, the contents of which are incorporated herein by reference discloses composite materials of silane modified polyaromatic polymers and bone. In some embodiments, silane-derivatized polymers may be used in composite materials instead of or in addition to first silanizing bone particles. In certain embodiments, polyurethanes and any copolymers used in accordance with the present inventions may not include silane modified polyaromatic polymers.

The active group of silanes may be incorporated directly into polymers or may be used to attach a second chemical group to bone particles. For example, if a particular monomer polymerizes through a functional group that is not commercially available as a silane, the monomer may be attached to the active group.

Non-silane linkers may also be employed to produce composite materials according to the invention. For example, isocyanates will form covalent bonds with hydroxyl groups on the surface of hydroxyapatite ceramics (de Wijn, et al., Fifth World Biomaterials Congress, May 29-Jun. 2, 1996, Toronto, Calif.). Isocyanate anchors, with tethers and active groups similar to those described with respect to silanes, may be used to attach monomer-analogs to bone particles or to attach chemical groups that will link covalently or non-covalently with a polymer side group. Polyamines, organic compounds containing one or more primary, secondary, or tertiary amines, will also bind with both the bone particle surface and many monomer and polymer side groups. Polyamines and isocyanates may be obtained from Aldrich.

Alternatively or additionally, biologically active compounds such as a biomolecule, a small molecule, or a bioactive agent may be attached to bone particles through a linker. For example, mercaptosilanes will react with sulfur atoms in proteins to attach them to bone particles. Aminated, hydroxylated, and carboxylated silanes will react with a wide variety functional groups. Of course, the linker may be optimized for the compound being attached to bone particles.

Biologically active molecules can modify non-mechanical properties of composite materials as they degrade. For example, immobilization of a drug on bone particles allows it to be gradually released at an implant site as a composite degrades. Anti-inflammatory agents embedded within composite materials will control inflammatory response long after an initial response to injection of the composite materials. For example, if a piece of the composite fractures several weeks after injection, immobilized compounds will reduce the intensity of any inflammatory response, and the composite will continue to degrade through hydrolytic or physiological processes. In some embodiments, compounds may also be immobilized on the bone particles that are designed to elicit a particular metabolic response or to attract cells to injection sites.

Some biomolecules, small molecules, and bioactive agents may also be incorporated into polyurethane matrices used in composite materials. For example, many amino acids have reactive side chains. The phenol group on tyrosine has been exploited to form polycarbonates, polyarylates, and polyiminocarbonates (see Pulapura, et al., Biopolymers, 1992, 32: 411-417; and Hooper, et al., J. Bioactive and Compatible Polymers, 1995, 10:327-340, the entire contents of both of which are incorporated herein by reference). Amino acids such as lysine, arginine, hydroxylysine, proline, and hydroxyproline also have reactive groups and are essentially tri-functional. Amino acids such as valine, which has an isopropyl side chain, are still difunctional. Such amino acids may be attached to the silane and still leave one or two active groups available for incorporation into a polymer.

Non-biologically active materials may also be attached to bone particles. For example, radiopaque, such as barium sulfate, luminescent (quantum dots), or magnetically active particles (iron oxide) may be attached to bone particles using the techniques described above. Mineralized bone particles are an inherently radiopaque component of some embodiments of present inventions, whereas demineralized bone particles, another optional component of composite materials, are not radiopaque. To enhance radiopacity of composite materials, mineralized bone particles can be used. Another way to render radiopaque the polymers utilized in accordance with the present inventions, is to chemically modify them such that a halogen, such as iodine, is chemically incorporated into the polyurethane matrices, as in U.S. patent application Ser. No. 10/952,202, now published as U.S. Patent Publication No. 20060034769, whose content is incorporated herein by reference.

If a material, for example, a metal atom or cluster, cannot be produced as a silane or other group that reacts with bone particles, then a chelating agent may be immobilized on bone particle surface and allowed to form a chelate with the atom or cluster. As bone particles and polymers used in the present invention are resorbed, these non-biodegradable materials may be removed from tissue sites by natural metabolic processes, allowing degradation of the polymers and resorption of the bone particles to be tracked using standard medical diagnostic techniques.

In some embodiments, bone particle surface is chemically treated before being mixed with polyurethane. For example, nondemineralized bone particles may be rinsed with phosphoric acid for 1 to 15 minutes in a 5-50% solution by volume. Those skilled in the art will recognize that the relative volume of bone particles and phosphoric acid solution (or any other solution used to treat bone particles), may be optimized depending on the desired level of surface treatment. Agitation will also increase the uniformity of the treatment both along individual particles and across an entire sample of particles. A phosphoric acid solution reacts with mineral components of bone particles to coat the bone particles with calcium phosphate, which may increase the affinity of the surface for inorganic coupling agents such as silanes and for polymer components of the composite material. As noted above, bone particle surface may be partially demineralized to expose the collagen fibers.

Collagen fibers exposed by demineralization are typically relatively inert but have some exposed amino acid residues that can participate in reactions. Collagen may be rendered more reactive by fraying triple helical structures of the collagen to increase exposed surface area and number of exposed amino acid residues. This not only increases surface area of bone particles available for chemical reactions but also for their mechanical interactions with polymers as well. Rinsing partially demineralized bone particles in an alkaline solution will fray collagen fibrils. For example, bone particles may be suspended in water at a pH of about 10 for about 8 hours, after which the solution is neutralized. One skilled in the art will recognize that this time period may be increased or decreased to adjust the extent of fraying. Agitation, for example, in an ultrasonic bath, may reduce the processing time. Alternatively or additionally, bone particles may be sonicated with water, surfactant, alcohol, or some combination of these.

In some embodiments, collagen fibers at bone particle surface may be cross-linked. A variety of cross-linking techniques suitable for medical applications are well known in the art (see, for example, U.S. Pat. No. 6,123,781, the contents of which are incorporated herein by reference). For example, compounds like 1-ethyl-3-(3-dimethylaminopropyl) carbodiimide hydrochloride, either alone or in combination with N-hydroxysuccinimide (NHS) will crosslink collagen at physiologic or slightly acidic pH (e.g., in pH 5.4 MES buffer). Acyl azides and genipin, a naturally occurring bicyclic compound including both carboxylate and hydroxyl groups, may also be used to cross-link collagen chains (see Simmons, et al, Biotechnol. Appl. Biochem., 1993, 17:23-29; PCT Publication WO98/19718, the contents of both of which are incorporated herein by reference). Alternatively or additionally, hydroxymethyl phosphine groups on collagen may be reacted with the primary and secondary amines on neighboring chains. Standard cross-linking agents such as mono- and dialdehydes, polyepoxy compounds, tanning agents including polyvalent metallic oxides, organic tannins, and other plant derived phenolic oxides, chemicals for esterification or carboxyl groups followed by reaction with hydrazide to form activated acyl azide groups, dicyclohexyl carbodiimide and its derivatives and other heterobifunctional crosslinking agents, hexamethylene diisocyanate, and sugars may also be used to cross-link collagens. Bone particles are then washed to remove all leachable traces of materials. In other embodiments, enzymatic cross-linking agents may be used. Additional cross-linking methods include chemical reaction, irradiation, application of heat, dehydrothermal treatment, and enzymatic treatments. One skilled in the art will easily be able to determine the optimal concentrations of cross-linking agents and incubation times for the desired degree of cross-linking.

Both frayed and unfrayed collagen fibers may be derivatized with monomer, pre-polymer, oligomer, polymer, initiator, and/or biologically active or inactive compounds, including but not limited to biomolecules, bioactive agents, small molecules, inorganic materials, minerals, through reactive amino acids on the collagen fiber such as lysine, arginine, hydroxylysine, proline, and hydroxyproline. Monomers that link via step polymerization may react with these amino acids via the same reactions through which they polymerize. Vinyl monomers and other monomers that polymerize by chain polymerization may react with these amino acids via their reactive pendant groups, leaving the vinyl group free to polymerize. Alternatively, or in addition, bone particles may be treated to induce calcium phosphate deposition and crystal formation on exposed collagen fibers. Calcium ions may be chelated by chemical moieties of the collagen fibers, and/or calcium ions may bind to the surface of the collagen fibers. James et al., Biomaterials 20:2203-2313, 1999; incorporated herein by reference. Calcium ions bound to the collagen provides a biocompatible surface, which allows for the attachment of cells as well as crystal growth. Polymer will interact with these fibers, increasing interfacial area and improving the wet strength of composite material.

In some embodiments, surface treatments of bone particles are optimized to enhance covalent attractions between bone particles and polyurethanes. In some embodiments, the surface treatment may be designed to enhance non-covalent interactions between bone particle and polyurethane matrix. Exemplary non-covalent interactions include electrostatic interactions, hydrogen bonding, pi-bond interactions, hydrophobic interactions, van der Waals interactions, and mechanical interlocking. For example, if a protein or a polysaccharide is immobilized on bone particle, the chains of polymer matrix will become physically entangled with long chains of the biological macromolecules when they are combined. Charged phosphate sites on the surface of bone particles, produced by washing the bone particles in basic solution, will interact with the amino groups present in many biocompatible polymers, especially those based on amino acids. The pi-orbitals on aromatic groups immobilized on a bone particle will interact with double bonds and aromatic groups of the polymer.

In some embodiments the substance delivered by DBM regions of the osteoimplant device may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, for example, SEMA3, controls vascular morphogenesis by inhibiting integrin function in the vascular system, and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anticholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-β); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

In one embodiment of an implant device comprising at least one cavity, it may be contemplated that any combination or mixture of same or different substances may be placed and retained therein, and further, different substances may be placed within the same or different cavities. In some embodiments, the allograft can be freeze dried before sterilization to both preserve growth factors/osteoinductivity and/or shelf life.

Sterilization

A medical implant device according to the present disclosure including its contents may be sterilizable. In various embodiments, one or more components of the implant device and/or its contents are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the medical device has gel components.

Other methods may also be used to sterilize the device and/or one or more components of the device and/or contents, including, but not limited to, gas sterilization, such as, for example, with ethylene oxide or steam sterilization.

Applications

An implant device according to the present disclosure may be configured for use in any suitable application. In some embodiments, the implant device may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. The implant device may be used in a minimally invasive procedure via placement through a small incision, via delivery through a tube, or other. The size and shape of the device may advantageously be designed in accordance with restrictions on delivery conditions.

In some embodiments, the implant device 10 of the present disclosure having osteoinductive material retained therein may be used to provide temporary or permanent fixation along an orthopedic target site. For example, the implant device 10 may be introduced into a facet joint while secured to a surgical insertion instrument and thereafter manipulated into the proper orientation before being released. According to one aspect, the implant device 10 may be introduced into a target site through use of any of a variety of suitable surgical instruments having the capability to engage the implant device 10. For example, a clinician may utilize the implant 10 in a minimally invasive facet joint fusion procedure. This approach requires removal of soft tissues from the facet joint and sliding in of the partially demineralized allograft disc. Even though the facet joint has a somewhat complicated surface geometry, the osteoimplant device shaped as a disc allows for an easy insert due to its partial flexibility resulting from the presence of demineralized regions on the outersurface of the disc. The amount of demineralization and the portion of the disc demineralized can be adjusted to give the disc just the right amount of flexibility and strength. The demineralized portion will begin facilitating new bone formation relatively quickly when compared to utilizing a solid nondemineralized cortical disc. The whole facet fusion process can thus be accelerated.

Although the disclosure has been described with reference to some embodiments, persons skilled in the art will recognize that changes may be made in form and detail without departing from the spirit and scope of the disclosure.

What is claimed is:

1. An osteoimplant device comprising: a body, which comprises a nondemineralized cortical bone, the nondemineralized cortical bone body includes a disc and at least one region comprising an enzymatically modified and ionically charged demineralized bone comprising a regular or irregular shape comprising an annular periphery, a substantially crescent shape periphery, a substantially semicircular shape periphery, a substantially O shape periphery or combinations thereof, wherein the implant device is formable into a shape and size configured for implantation at a surgical site, and wherein the at least one region of demineralized bone comprises demineralized bone fibers and demineralized bone chips in a ratio of from about 25:75 to about 75:25 fibers to chips and at a depth of from about 50 microns to about 5000 microns, and the osteoimplant comprises a compressive modulus of from about 2,000 MPa to 3,800 MPa and exhibits resiliency and flexibility of from about 10 degree to about 45 degree angles.

2. An osteoimplant device of claim 1, wherein the implant device is configured as a disc having upper and lower surfaces, which are surface demineralized and the osteoimplant is a composite.

3. An osteoimplant device of claim 1, wherein the nondemineralized cortical bone comprises cortical bone allograft or xenograft in an amount from about 5 wt % to about 95 wt %, from about 15 wt % to about 85 wt %, from about 25 wt % to about 75 wt %, or from about 35 wt % to about 65 wt % and the osteoimplant is a monolithic osteoimplant.

4. An osteoimplant device of claim 1, wherein the volume of demineralized bone to cortical bone in the osteoimplant device is from about 40 vol % to about 80 vol %, or from about 50 vol % to about 70 vol %.

5. A osteoimplant device of claim 1, wherein the composite osteoimplant device is configured to increase the area of contact to a host bone from about 5% to about 60%, or from about 10% to about 30%.

6. An osteoimplant device of claim 5, wherein the host bone is a facet joint.

7. An osteoimplant device of claim 1, wherein the shape of the osteoimplant comprises regular or irregular shapes including disc, dome, doughnut, shapes configured for facet joint fusion, shapes configured for posterior lumbar interbody fusion, shapes configured for anterior lumbar interbody fusion or shapes configured for anterior cervical disectomy and fusion.

8. An osteoimplant device of claim 1, wherein the demineralized bone is enzymatically modified with at least one enzyme comprising cysteine proteinases, matrix metalloproteinases, enzymes comprising amylases, lipases, pectinases, cellulases, hemicellulases, pentosanases, xylanases, phytases or combinations thereof.

9. A method of treating a patient having a bone defect in a host bone comprising inserting the device of claim 1 into the bone defect.

10. A method of claim 9, wherein the body of nondemineralized cortical bone contacts load bearing bone tissue of the host bone and the at least one region comprising demineralized bone contacts non-load bearing bone tissue of the host bone.

11. A disc spacer having a core of nondemineralized cortical bone and an outer surface surrounding the core, the outer surface including at least one region comprising an enzymatically modified and ionically charged demineralized bone with at least one enzyme comprising cysteine proteinases, matrix metalloproteinases, enzymes comprising amylases, lipases, pectinases, cellulases, hemicellulases, pentosanases, xylanases, phytases or combinations thereof, wherein the demineralized bone comprises demineralized bone fibers and demineralized bone chips in a ratio of from about 25:75 to about 75:25 fibers to chips and at a depth of from about 50 microns to about 5000 microns, and the osteoimplant comprises a compressive modulus of from about 2,000 MPa to about 3,800 MPa and exhibits resiliency and flexibility of from about 10 degree to about 45 degree angles.

12. A disc spacer of claim 11, wherein the implant is configured for insertion into a facet joint.

13. A disc spacer of claim 11, wherein the at least one region comprising demineralized bone is a regular or irregular shape in a pattern comprising an annular periphery, oblong, circular, curved, triangular, zigzag, substantially crescent, substantially semicircular, substantially O shaped, star, substantially claw-shaped or combinations thereof.

14. A disc spacer of claim 11, wherein the volume of demineralized bone to cortical bone in the implant device is from about 40 vol % to about 80 vol %, or from about 50 vol % to about 70 vol %.

15. A disc spacer of claim 11, wherein the nondemineralized cortical bone comprises cortical bone allograft or xenograft in an amount from about 5 wt % to about 95 wt %, from about 15 wt % to about 85 wt %, from about 25 wt % to about 75 wt %, or from about 35 wt % to about 65 wt %.

16. A disc spacer of claim 11, wherein the disc spacer is configured to increase the area of contact to the host bone from about 5% to about 60%, or from about 10% to about 30%.

17. A disc spacer having a core of nondemineralized cortical bone and an outer surface surrounding the core, the core comprising a regular or irregular shape capable of separating the outer surface into multiple regions, the outer surface having an inner region contacting the core comprising regular or irregular shape comprising an annular periphery, a substantially crescent shape periphery, a substantially semicircular shape periphery, a substantially O shape periphery or combinations thereof, the outer surface comprising a regular or irregular shape in a pattern comprising an annular periphery, oblong, circular, curved, triangular, zigzag, substantially crescent, substantially semicircular, substantially O shaped, star, substantially claw-shaped or combinations thereof, the outer surface including at least one region comprising an enzymatically modified and ionically charged demineralized bone with at least one enzyme comprising cysteine proteinases, matrix metalloproteinases, enzymes comprising amylases, lipases, pectinases, cellulases, hemicellulases, pentosanases, xylanases, phytases or combinations thereof, wherein the disc spacer exhibits resiliency and flexibility of from about 10 degree to about 45 degree angles.

* * * * *